(12) United States Patent
Brusky (10) Patent No.: US 10,168,688 B2
(45) Date of Patent: Jan. 1, 2019

(54) SYSTEMS AND METHODS FOR IMPLEMENTING A POINTER-GUIDED TRACKING SYSTEM AND A POINTER-GUIDED MECHANICAL MOVABLE DEVICE CONTROL SYSTEM

(71) Applicant: Taylor Brusky, New Hope, PA (US)

(72) Inventor: Taylor Brusky, New Hope, PA (US)

(*) Notice: Subject to any disclaimer, the term of this patent is extended or adjusted under 35 U.S.C. 154(b) by 109 days.

(21) Appl. No.: 15/582,684

(22) Filed: Apr. 29, 2017

(65) Prior Publication Data

US 2017/0315536 A1 Nov. 2, 2017

Related U.S. Application Data

(60) Provisional application No. 62/330,031, filed on Apr. 29, 2016.

(51) Int. Cl.
| | | |
|---|---|---|
| *G05B 19/409* | (2006.01) | |
| *A61B 90/50* | (2016.01) | |
| *A61B 34/30* | (2016.01) | |
| *B25J 9/16* | (2006.01) | |
| *G06F 3/16* | (2006.01) | |
| *G05B 19/402* | (2006.01) | |
| *G05B 19/4061* | (2006.01) | |
| *B25J 13/00* | (2006.01) | |

(Continued)

(52) U.S. Cl.
CPC ............ *G05B 19/409* (2013.01); *A61B 34/30* (2016.02); *A61B 90/50* (2016.02); *B25J 9/1676* (2013.01);

(Continued)

(58) Field of Classification Search
CPC ......................... G05B 19/409; G05B 19/0423; G05B 19/402; G05B 19/4061; G05B 2219/40623; G05B 2219/23386; G05B 2219/42288; B25J 9/1676; B25J 13/003; G06F 3/167; A61B 90/50; A61B 34/30; A61B 2017/00203; A61B 17/00; A61B 2090/502

(Continued)

(56) References Cited

U.S. PATENT DOCUMENTS

| 6,368,332 B1 * | 4/2002 | Salcudean ............... A61B 90/50 128/897 |
|---|---|---|
| 7,038,699 B2 * | 5/2006 | Sato ....................... H04N 5/222 345/427 |

(Continued)

*Primary Examiner* — Jaime Figueroa
(74) *Attorney, Agent, or Firm* — TannerIP PLLC; Daniel A. Tanner, III; James A. Golladay, II (57) ABSTRACT

A system and method are provided for facilitating hands free and precise movement, translation and repositioning of a movable mechanical apparatus, including an operating room lighting system, mounted to a mechanically-movable base component including, for example, an articulable or articulated robotic-type arm, according to user input pointing commands, including laser or other like pointing commands initiated by a user. The user provides hands free designation of a point of focus with a pointing device. A sensor associated with the movable mechanical apparatus automatically detects the designated point of focus and a processor determines and executes a scheme of movement for moving the movable mechanical apparatus from a current position to a position proximate to the designated point of focus. A collision avoidance scheme is also provided for safety and to alert the user as to the presence of any impediment in the determined scheme of movement.

20 Claims, 4 Drawing Sheets

(51) Int. Cl.
*G05B 19/042* (2006.01)
*A61B 17/00* (2006.01)

(52) U.S. Cl.
CPC ........ *B25J 13/003* (2013.01); *G05B 19/0423* (2013.01); *G05B 19/402* (2013.01); *G05B 19/4061* (2013.01); *G06F 3/167* (2013.01); *A61B 17/00* (2013.01); *A61B 2017/00203* (2013.01); *A61B 2090/502* (2016.02); *G05B 2219/23386* (2013.01); *G05B 2219/40623* (2013.01); *G05B 2219/42288* (2013.01)

(58) Field of Classification Search
USPC ................................................ 700/245, 262
See application file for complete search history.

(56) References Cited

U.S. PATENT DOCUMENTS

| | | | | |
|---|---|---|---|---|
| 7,714,895 B2* | 5/2010 | Pretlove | ................. | B25J 9/1656 348/115 |
| 8,880,222 B2* | 11/2014 | Kawamoto | ............ | B25J 9/1664 318/568.12 |
| 9,186,793 B1* | 11/2015 | Meier | .................... | B25J 9/1694 |
| 9,943,372 B2* | 4/2018 | Sholev | ............... | A61B 1/00016 |
| 2006/0202953 A1* | 9/2006 | Pryor | ..................... | A63F 13/02 345/156 |
| 2010/0082118 A1* | 4/2010 | McGreevy | ......... | G05B 19/4183 700/17 |
| 2011/0245974 A1* | 10/2011 | Kawamoto | ............ | B25J 9/1664 700/259 |
| 2012/0092485 A1* | 4/2012 | Meinherz | ................ | F16P 3/142 348/91 |
| 2012/0095575 A1* | 4/2012 | Meinherz | ........... | G05B 19/4061 700/79 |
| 2012/0209428 A1* | 8/2012 | Mizutani | .............. | G05B 19/423 700/250 |
| 2015/0258682 A1* | 9/2015 | Izikevich | ............... | B25J 9/0009 700/245 |
| 2015/0258683 A1* | 9/2015 | Izhikevich | ............... | B25J 9/163 700/250 |
| 2016/0096272 A1* | 4/2016 | Smith | ...................... | B25J 9/163 700/253 |
| 2016/0113728 A1* | 4/2016 | Piron | ................. | A61B 17/3421 606/130 |

\* cited by examiner

SYSTEMS AND METHODS FOR IMPLEMENTING A POINTER-GUIDED TRACKING SYSTEM AND A POINTER-GUIDED MECHANICAL MOVABLE DEVICE CONTROL SYSTEM

This application claims the benefit on U.S. Provisional Patent Application No. 62/330,031 entitled "Systems and Methods for Implementing a Laser-Guided Tracking System And Laser-Guided Movable Lighting Control System," filed on Apr. 29, 2016, the disclosure of which is hereby incorporated by reference herein in its entirety.

BACKGROUND

1. Field of the Disclosed Embodiments

This disclosure is directed to a unique set of structural features that cooperate to provide, in exemplary embodiments, automated systems, methods, techniques, processes, products and product components to facilitate hands free and precise translational movement, and repositioning of a movable mechanical device, including an operating room lighting system, mounted to a mechanically-movable base component including, for example, an articulable or articulated robotic-type arm, according to user input pointing and voice commands, including laser or other like pointing commands initiated by a user.

2. Related Art

Mechanical (or robotic) arm-mounted components and/or devices come in many configurations directed to many and widely varied utilities and/or functions, often in "sterile" environments, or in hazardous material handling environments. Mechanically-movable base components, including robotic arms, often mount tools and devices for implementing manufacturing and object forming functions including cutting tools, shaping tools, welding tools and the like. Mechanically-manipulable arm-mounted lighting systems are often found in, for example, medical facilities, including operating rooms, and in other task-related environments in which precise positioning of illuminating components are an advantage. A specific benefit of employing mechanical (or robotic) movable base or arm-mounted components is found in an ability of the arm (or other mechanically-adjustable base component) to generally reposition a tool, implement or device mounted to it, including at a relative distal end of a mechanical arm, to any position according to the range of motion and degrees of freedom available through use of the mechanical arm or other mechanical base component. Positioning may be precise and repeatable. In many arm-type implementations, virtually limitless three-dimensional repositioning and pointing of an apparatus, tool, implement, device, lighting component or the like mounted on the mechanical arm or base is available.

Conventionally, movement of arm-mountable mechanisms, machines, tools, implements, devices or components occurs according to one or more operating techniques. These include, but are not limited to, (1) manual manipulation of the arm or arm-mounted component by a user, (2) remote control, directed and/or automated manipulation of the arm or arm-mounted component initiated by a user at a control console, often using some manner of joystick controller, or through user interaction with a touchscreen display, and/or (3) powered manipulation of the arm or the arm-mounted component according to a pre-determined program, or pre-programmed scheme of movement (often used to control, for example, a robotic arm in a repetitive assembly-line type manufacturing process). In current surgical lighting and like implementations, manual repositioning of a lighting component mounted to a generally counterbalanced, but non-powered, arm represents a standard practice.

An analysis of particular use cases of an arm-mounted configuration for movable components, such as a surgical lighting array reveals typical shortfalls that may be encountered in a spectrum of conventional operational implementations and use cases for user-controlled positioning of mechanical base-mounted or arm-mounted implements. Generally, manual manipulation may involve disturbing the concentration of the user in focusing on her or his primary objective or task. Joystick or other user-aided control of the mechanical manipulation of the mechanical implements translated through the movable base or movable arm aid in relieving detailed mechanical movement of the implements, but still require separate concentration of either the primary user, or a user assistant, in ensuring that the mechanical implement is precisely positioned according to the desired use. In an operating room scenario, the user or the user assistant may be one or more members of the surgical staff.

In conventional implementations, surgical lighting may, for example, be mounted for use on a floor stand, which may be stationary or mobile. Alternatively, to reduce clutter on the floor of the operating theater, the surgical lighting may typically be mounted to an articulable mechanical (or robotic) arm, or other mechanically-movable base structure. The arm or base structure, in turn, may be anchored to a wall or ceiling of the operating theater. Even with the illumination available from a comparatively high intensity lighting system that can be generally manually pointed directly at a particular area under consideration, many surgeons separately choose to supplement the lighting of the operative field of a particular patient, or in a particular procedure, by employing one or more of a headlamp and a surgical loupe with a light attachment.

As technologies advance, many operating theaters are integrating technologic developments to produce what are commonly referred to as "integrated operating rooms" and/or "hybrid operating rooms." These operating rooms may include automated robotic X-ray machines, robotic operating tables and other automated and/or cooperating units. These operating rooms may also include more advanced lighting systems that are of a type referred to briefly above as being controlled by a joystick type controller, via a touch screen or according to voice commands from a user. The different robotic components must be positioned precisely with respect to one another in order to obtain maximum effectiveness with regard to their use in support of, for example, efficient and effective surgical operations.

The particular use case of surgical lighting in an operating room environment or operating theater highlights what may be considered to be shortfalls associated specifically with employment of such movable or powered structures in the hospital operating room. Overhead lighting, for example, comes with attendant risks to the patient, which manipulation of the mechanical structure may introduce. In manual manipulation of commonly-employed surgical lighting, for example, dust, paint chips and other debris may be generated and fall from clunky movements of the arm to which the surgical lighting is mounted.

Loose debris material can lead to an unsterile environment and surgical site contamination that may infect the patient. Substantial costs and additional risks are associated with inadvertently inducing such a surgical site infection.

Surgical site infections, which occur in the part of the body that is compromised by the surgical procedure, may arise in the skin, tissue, in organs, or in implants, and can lead to prolonged hospital stays, and/or increased risk of patient mortality associated with any surgical procedure, the increase in risk being, in instances, more than tenfold. The incidents of surgical site infection may double a hospital's cost of treatment as the estimated cost per infection can range from $11,000-$35,000. Estimates of a total cost in the United States alone associated with this additional risk range from $3 billion-$10 billion annually.

Vigilance with respect to a recognized potential for inducing contamination has conventionally led to a number of mitigating actions, including recalls on lamps due, for example, to the paint on them having chipped and become dislodged from being repeatedly manually manipulated, and impacting other structures. The lamps themselves, and the apparatus to which the lamps are attached, are cleaned before each procedure, but according to the Association of Perioperative Registered Nurses and various textbooks addressing the matter, turbulent air flow and dust on lamps remains an issue that may contribute to surgical site infection when it is dislodged through the multiple manual manipulations of the lighting structure during the surgical procedure.

Moreover, having to touch the light to manually move, or manipulate, the light for preferable or optimal illumination of the surgical field, particularly when multiple movements are required to optimally position the illumination source, poses a number of risks to the sterility of the process and to the individual handling the movement of the light. Even the handles by which the surgical lights are specifically manipulated are at risk of becoming non-sterile during a surgical evolution by something as simple as, for example, being inadvertently bumped by the head of a surgeon or surgical team staff member. Consider that an assisting nurse may come in contact with a non-sterile part of the patient (mouth, nose, throat, gastrointestinal tract and the like) and then touch the light handle. A result is that the potential for extensive contamination of the surgical field is increased.

As noted briefly above, with every separate movement of the mechanical apparatus, the necessity to manually manipulate the lighting structure multiple times during a particular procedure can significantly increase the risk for patient infection. One study from the Department of Biomechanical Engineering at Delft University of Technology in the Netherlands showed that, on average, every 7.5 minutes during a surgical procedure, a luminaire action (LA) takes place. Some 64% of these adjustments are estimated to involve interruption of the surgical tasks of the operating room staff while the adjustments are being made. The number and extent of adjustments to obtain and maintain an optimally well-lit surgical field, illumination intensity, absence of shadowing, and direct penetrating illumination of a full depth of a deep wound are all considered as most frequently indicated lighting aspects that are noted as areas rife for improvement.

The above-outlined use case pertaining to a hospital operating room is particularly instructive in highlighting difficulties associated with manual manipulation of mechanically mounted devices and implements. Certain of the difficulties outlined above are, however, not limited to only operating rooms in hospitals. There are myriad mechanically-aided tasks that may benefit from a more advanced and more precise user-controlled manipulation of a powered mechanical base unit or a powered mechanical articulating arm to which a particular mechanical implement may be mounted for the safe and efficient completion of mechanically-assisted tasks.

SUMMARY OF DISCLOSED EMBODIMENTS

In view of the above outlined, and other shortfalls, in conventional schemes for remotely controlling mechanical implements, devices and/or tools, it would be advantageous to provide an advanced system for allowing an operator to precisely position a mechanical implement, device and/or tool mounted on a moving base, or at a distal end of a mechanically-articulable arm, while the operator maintains focus on an area of operation or "aim point" for the action of the mechanical implement, device and/or tool.

Exemplary embodiments of the systems and methods according to this disclosure may provide a unique combination of an operator-controlled pointing element, a pointing element (or aim point) detecting device, and a processor-implemented control scheme that translates a detected point of focus of the pointing element into mechanical movement of a base-mounted or articulating arm-mounted mechanical implement, device and/or tool device for precise positioning in accordance with the focus of the operator-controlled pointing element.

Exemplary embodiments may enhance integrated operating rooms, which may represent a unique operational scenario to which the disclosed systems and methods may be advantageously applied, by providing a closed-loop processor-controlled scheme for directing repositioning of lighting and other integrated systems in the operating room according to commands provided by a surgeon, or surgical assistant, through the employment of a wearable pointing device.

In embodiments, surgeons and surgical nurses may represent a population of targeted end users that may benefit from the pointing-device centered mechanical remote control schemes according to this disclosure, including those for providing automated re-positioning of operating room lighting components.

Exemplary embodiments may include certain line of motion sensing input devices that may be particularly configured to detect an illuminated, or otherwise designated, aim point for focus of a mechanical implement mounted to a movable base or articulated arm in order to "sense" a point of focus for the mechanical implement and to provide input to a processor-controlled scheme for converting the "sensed" point of focus for the mechanical device into commands for moving the mechanical device to a position proximate to that point of focus.

In embodiments, proximate sensing in a vicinity of the mechanical implement may be provided by implement mounted sensors, or otherwise, to limit or eliminate a potential for the collision of the mechanical implement with any obstruction during the scheme of movement of the mechanical implement.

Exemplary embodiments may further enhance new and unique opportunities for technology insertion into an integrated operating room providing a capacity whereby mechanical movement of supporting structures, including lighting, may be directed without a break in concentration from the task at hand for the operator directing that mechanical movement, including the surgeon, or any member of the surgical staff.

Exemplary embodiments may incorporate voice command technology to direct acquisition of the point of focus of the pointing device by a sensing device configured to acquire information regarding the point of focus, and separately to initiate processing of the point of focus information in order to direct the processor-controlled scheme whereby the mechanical implement is directed toward, or to, the point of focus identified by the pointing device.

Exemplary embodiments may provide a unique interactive automated system for particularly directing movement, translation and/or re-positioning of an implement, tool, apparatus or the like, including a lighting source for directing light to an area of interest, through automated and/or powered manipulation of a motorized base component, including a mechanical (or robotic) arm.

Exemplary embodiments may provide a unique manner by which a user may direct movement of any tool, implement, apparatus or structure, including a directed lighting system, mounted on a movable base to a point of focus for the tool, implement, apparatus or structure.

Exemplary embodiments may provide a lighting system that may be mounted on a motorized platform including, for example, mechanical (or robotic) arm for directing illumination produced by the lighting system at a particular point of focus, and from a particular aspect.

Exemplary embodiments may provide a user with unique capacity by which to identify the particular point of focus using any manner of pointing device, including a wearable pointing device, which may include an illuminated spot pointing system, a laser spot pointing system, a mechanical pointing component or other like pointing device.

Exemplary embodiments may provide direct automated positioning of a particular mechanical implement mounted to a motorized base, including direct automated positioning of illumination from a lighting source at a particular point of focus using voice commands, which may additionally modify a direction from which the illumination is projected at the particular point of focus.

Exemplary embodiments may provide at least one sensor associated with the motorized platform, the at least one sensor being used to sense a targeted position or aim point to which the pointing device, including a point of focus of an illuminating laser spot produced by a laser spot pointing system, may be directed.

Exemplary embodiments may generate commands to direct movement of the motorized platform such that the mechanical implement mounted to the motorized platform, including but not limited to, illumination produced by a mounted lighting system lighting system, is directed particularly for use, including illumination of the point of focus identified by the location of a laser spot.

In embodiments, virtually any tool, implement, apparatus or structure that may be mountable to a distal end of an articulated mechanical (or robotic) arm, or may otherwise be mounted to a movable base component, may be directed as described above with respect to the illumination produced by a directed lighting system.

These and other features, and advantages, of the disclosed systems and methods are described in, or apparent from, the detailed description of various exemplary embodiments discussed below.

BRIEF DESCRIPTION OF THE DRAWINGS

Various exemplary embodiments of the disclosed systems and methods for providing a unique set of structural features that cooperate to provide automated systems, methods, techniques, processes, products and product components to facilitate hands free and precise movement, translation and repositioning of a movable mechanical apparatus, including an operating room lighting system, mounted to a mechanically-movable base component including, for example, an articulable or articulated robotic-type arm, according to user input pointing commands, including laser or other like pointing commands initiated by a user, will be described, in detail, with reference to the following drawings, in which.

DETAILED DESCRIPTION OF EMBODIMENTS

The disclosed systems and methods provide for integration of a unique set of structural features that cooperate to provide automated systems, methods, techniques, processes, products and product components to facilitate hands free and precise movement, translation and repositioning of a movable mechanical apparatus, including an operating room lighting system, mounted to a mechanically-movable base component including, for example, an articulable or articulated robotic-type arm, according to user input pointing commands, including laser or other like pointing commands initiated by a user. Certain real-world applications described above, and as will be referred to in further detail below, provide exemplary operating scenarios in which the systems and methods according to this disclosure may be particularly advantageously employed. These real-world applications for the disclosed mechanical component repositioning, control and collision avoidance schemes should not be considered as limiting the described systems and methods in any particular manner. Rather, the disclosed embodiments are intended to provide an overview of a particular system architecture that may be implemented to autonomously move one or more mechanical components mounted to one or more translatable base units in support of any one of a number of device-implemented tasks.

It should be appreciated that precise movement and positioning functions that may be facilitated through implementation of the disclosed schemes may enhance safety with respect to those precise movement and positioning functions, as well as safety and security of the tasks that those precise movement and positioning functions support, and in the environments in which those movement and positioning functions are implemented. In this regard, broad application of the disclosed schemes for providing a new and unique remote-control methodology that allows a user to maintain her or his focus on a particular point of interest for the task at hand may advantageously benefit the efficiency, effectiveness, safety, security and precise completion of the assigned and/or supported tasks.

Reference will be generally made to a specific use case in which the disclosed schemes may be particularly advantageously employed in assisting a surgeon in precisely, expeditiously, and safely repositioning of operating room lighting mounted to a motor-controlled base structure or articulated robotic arm. All such references are intended to be illustrative only and not limiting the subject matter of this disclosure to any particular use case, any particular class of pointing devices or components, any particular sensors for cooperatively detecting a point of focus to which the pointing devices or components may be directed, or to any particular class of mechanical implements that may be mounted to a movable base for use. Any application of the systems and methods according to this disclosure that may beneficially increase the precision with which a particular mechanical implement is repositioned is contemplated as being within the scope of the disclosed schemes.

In this regard, the disclosed systems and methods for directing various tools, implements, apparatus or structures mounted on mechanically-movable bases based on sensing any form of an externally-indicated position including designation by any manner of a pointing device, e.g. an illuminating spot or laser spot position indicator, interpreting (or converting) sensed aim point information to a scheme for mechanical motion of the tools, implements, apparatus or structures, and effecting such a movement scheme according to the interpretation of the sensed aim point information are intended to be broadly described. Reference to these specific utilities for the disclosed systems, methods, processes, techniques and/or schemes of movement are intended to provide real-world operating scenarios that will assist the reader in understanding the general scope of the disclosed schemes and particularly beneficial tasks in which those schemes may be advantageously employed.

Exemplary embodiments described and depicted in this disclosure should not be interpreted as being specifically limited to any particular configuration of (1) a mechanically-articulable base component, including restriction to, for example, an articulated mechanical (or robotic) arm, (2) any particular pointing or illumination source for identifying a targeted position to which an apparatus mounted on the mechanically-articulable base component may be directed, (3) any particular sensor component for sensing an aim point, including an illuminated spot, to which to direct a particular apparatus through movement of the mechanically-articulable base component, (4) to any particular tool, implement, apparatus or structure mounted on the mechanically-articulable base component or (5) any particular control and/or processing components or schemes for directing and/or controlling movement of the tool, implement, apparatus or structure through the of the mechanically-articulable base component. It should be recognized that any advantageous use of schemes for moving implements attached to a mechanically-articulable base component, including directed lighting components mounted to mechanical arms, based on sensing a designated point source, including a point source of illumination, to target a point for focus of the implement, which employs devices and/or methods such as those presented in this disclosure is contemplated as being included within the scope of the disclosed exemplary systems and methods.

A particular embodiment of a line of motion sensing input device may be according to that marketed as Microsoft® Kinect that is centered around a webcam-style add-on peripheral to enable users to control and interact with gaming consoles and/or computers as a replacement for, or supplement to, a more conventional, or traditional, game controller. The line of motion sensing input may be obtained through a user interface interpreting combinations of gestures and spoken commands to implement operational control of a particular automated system. Again here, this particular technology is intended to represent both one possible implementation whereby the line of motion sensing may be implemented.

Voice command technology too, particularly as employed in a surgical setting has been developing slowly and for decades. An example of an in-use system may be Stryker Corporation's presented Hermes®, which is essentially a voice command operating suite. With Hermes®, the surgeon may employ a voice command card that the surgeon has pre-programmed with particular commands that the surgeon may desire to use during implementation of a particular surgical operation. Employing this, or a like, system, surgeons may, for example, direct certain aspects of an operation according to those pre-programmed commands. Again here, this is but one example of a particular commercial-off-the-shelf (COTS) voice command product that may be advantageously employed in the integrated systems and methods according to this disclosure.

Figure 1:
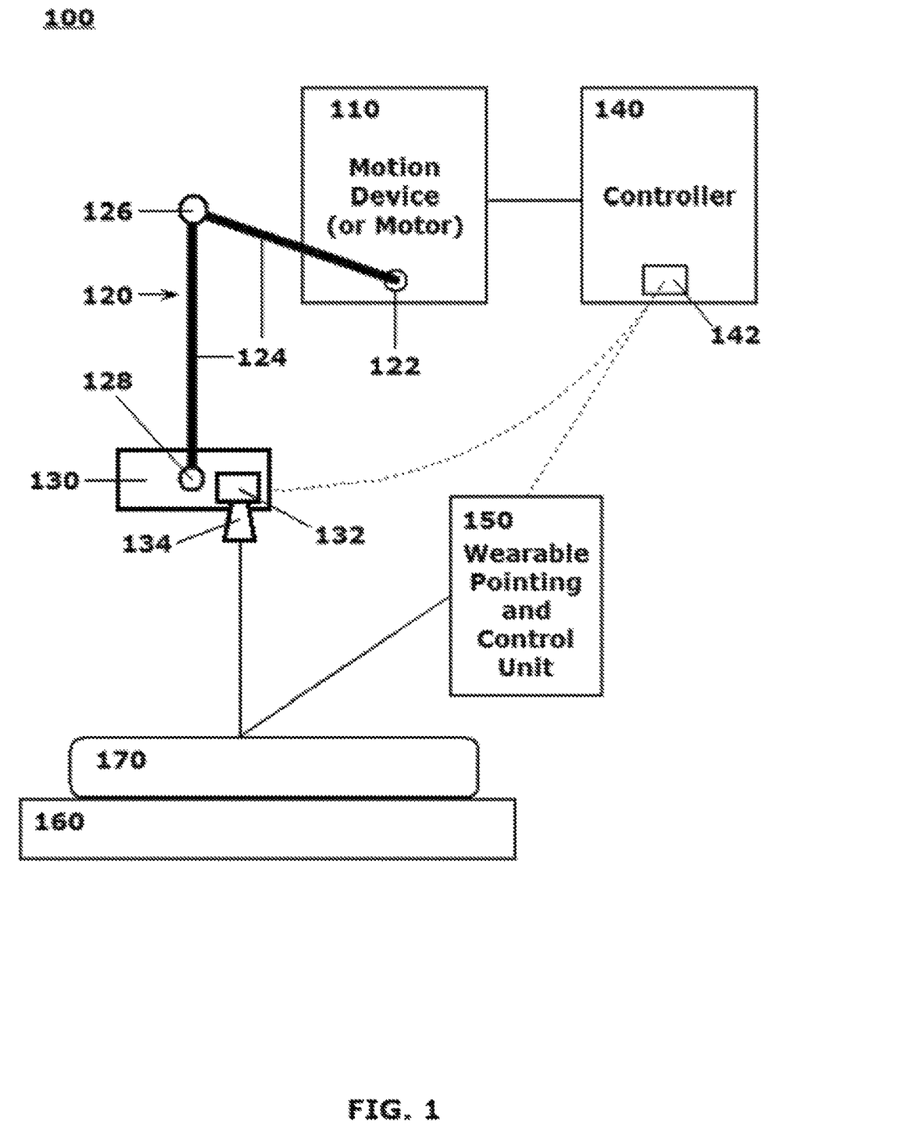
FIG. 1 illustrates a schematic diagram of an exemplary mechanical device movement system according to this disclosure.

FIG. 1 illustrates a schematic diagram of an exemplary mechanical device movement system 100 according to this disclosure. As shown in FIG. 1, the exemplary system 100 may include a motion device (or motor) 110 that may be usable to control the movement of an exemplary mechanically-articulable arm structure 120.

The mechanically-articulable arm structure 120 may include, for example, a plurality of movable arm component structures 124 that are movably anchored at a proximal end of the mechanically-articulable arm structure 120 to the motion device (or motor) 110 at a connection point 122. The mechanically-articulable arm structure 120 may further include at least one joint 126 between a first one of the plurality of movable arm component structures 124 and a second one of the plurality of movable arm component structures 124. The mechanically-articulable arm structure 120 may further comprise a plurality of actuators (not shown) for directing translational movement of the distal end of the mechanically-articulable arm structure 120 through a range of motions in multiple axes.

The mechanically-articulable arm structure 120 may have mounted at a distal end one or more selectable implements 130 as enumerated in the various listings of tools, implements and/or devices enumerated above. Each specific selectable one of the one or more selectable implements 130 may have associated with them one or more sensor elements 134 and a communication device 132. If the communication device 132 is in the form of a wired communication device, the wiring for communication between the communication device 132 and a controller 140 may be via wiring that is routed internally through the mechanically-articulable arm structure 120. If the communication device 132 is in the form of a wireless communication device, such communication device 132 may be usable to transmit signals to a wireless receiver component 142 associated with the controller 140. In embodiments, the communication device 132 and the sensor element 134 may be separately mounted to the mechanically-articulable arm structure 120, or may be mounted separately from the mechanically-articulable arm structure 120 as one or more proximate sensor components 134 capable of acquiring an aim point designation with regard to a pointing unit as will be described in greater detail below.

In operation, a user such as, for example, a surgeon or other operator, may be able to position overhead lighting using a wearable pointing and control unit 150. The wearable pointing and control unit 150 may be usable to direct, for example, a mechanical pointer, or a spot of laser energy at a particular point of interest on a body structure 170 under consideration, the body structure 170 being positioned on a fixed or movable base structure 160.

The wearable pointing and control unit 150 may be in a form of, for example, an exemplary head gear as will be described in greater detail with respect to the depiction in FIG. 2 below. In operation, the wearable pointing and control unit 150 may be usable to designate a particular point of focus for the movement of the one or more selectable implements 130 proximate to the particular point of focus while the operator using the wearable pointing and control unit 150 may maintain her or his concentration on the particular point of focus for the task at hand.

Figure 2:
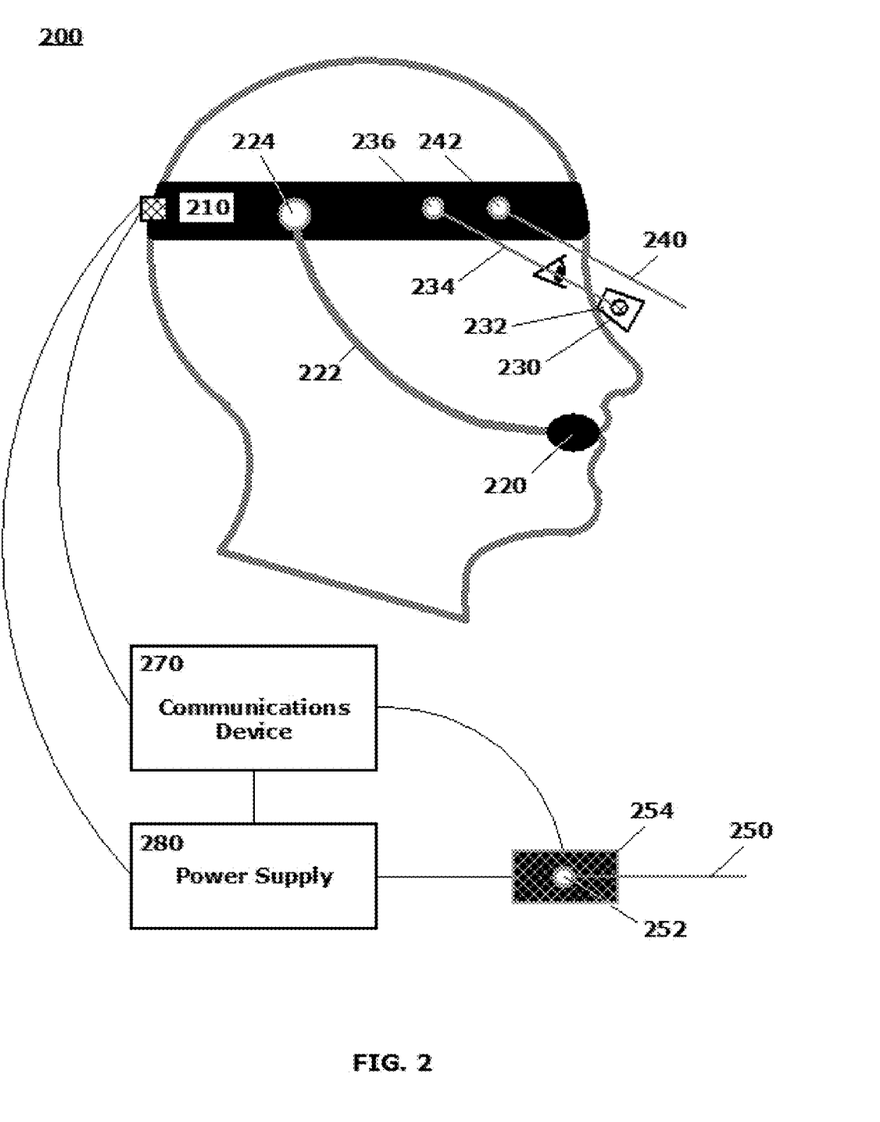
FIG. 2 illustrates a schematic diagram of exemplary embodiments of wearable pointing and communicating devices usable with the systems and methods according to this disclosure.

FIG. 2 illustrates a schematic diagram of exemplary embodiments 200 of wearable pointing and communicating devices usable with the systems and methods according to this disclosure. As shown in FIG. 2, an operator may don a wearable pointing and communicating device in the form of a headband 210 to which multiple communicating and control devices may be mounted for use.

A microphone 220 may be provided supported by a boom 222 connected to the headband 210 at an attachment point 224 to provide a mechanism whereby a user may provide voice commands to a control system via a communications device 270, the communications between the microphone 220 in the communications 270 may be via wired or wireless communication schemes.

An aiming reticle or surgical loupe 230 may be provided. The aiming reticle or surgical loupe 230 may be connected to the headband 210 via an adjustable mounting bar 234 having an adjustable connection point 232 at a distal end and a headband attachment point 236 at a proximal end facilitate operator comfort and a full range of adjustment of the aiming reticle or surgical loupe 230 with respect to the headband 210.

A pointing device 240 may be provided in alignment with the adjustable mounting bar 234 and attached to the headband 210 via an attachment point 242. The pointing device may be in the form of a mechanical pointer with a particular configuration at a distal end such that the distal and can be independently tracked by a sensor component such as that shown in FIG. 1. The pointing device may be in the form of an illuminating light emitting or laser spot committing component that may provide the user wearing the wearable pointing and communicating device may position and illuminating laser spot at a particular point of focus such that the sensor in the form of a laser spot tracker, for example, may ascertain information regarding the particular point of focus identified by the pointing device.

According to a control scheme that will be described in greater detail below, voice commands may be issued via the microphone 220 and interpreted by the communications device 270 in order that the movement of the mechanical implement is restricted only to those movements that the operator chooses to designate through voice commands. In other words, random movement of the mechanical implement following a sensed position of the pointer may be restricted by being only executable on issuance of a particular voice command by the user.

A separate power supply 280 may be provided to power one or more of the communications device 270, microphone 220 or pointing device 240, as appropriate.

The exemplary head gear mounted design may be supplemented or otherwise augmented through use of a separately wearable pointing device 250 which may be in a same form as the pointing devices 240 described above but which may be mounted to a ring or bracelet apparatus 254 to be separately worn by the operator on a wrist or finger, for example, the pointing device 250 being attached to the ring or bracelet apparatus 254 at an attachment point 252 in the same manner as described above with respect to the headband 210. In embodiments in which the pointing device 240 or 250 may be in a form of a laser pointer device associated wiring may be provided to connect the laser pointer device to the power supply 280.

In embodiments, the pointing device 240, 250 may be removably mounted, substantially in the manner shown, as a portion of the exemplary head gear or other wearable component to allow substantially hands-free movement of the pointing device 240, 250 by the user, including by a surgeon, to direct an emitted beam of laser energy from a laser-configured pointing device to a point of for movement of the mechanical implement according to the disclosed sensing and movement schemes.

While depicted as integral to, or attachable to, the headband 210, it should be appreciated that the microphone 220 may be separately accommodated in the area around the operator to obtain operating commands via any manner of proximately located wired or wireless microphone by which the user may communicate verbal commands for operation of the system in the manner that will be further described in detail according to the control scheme outlined below.

In operation, a surgeon may wear the exemplary headband 210 with pointing device 240 in a form of a laser pointer attached to the headband 210. The laser pointer may be positioned at a precise angle in order for the surgeon to accurately point with it. When the surgeon wants to move the light to a specific area, the surgeon may issue a verbal command such as, for example, "LASER ON." The surgeon may look at the spot that the surgeon intends to be targeted by the illumination and confirm positioning of the illumination target by, for example, issuing a separate voice command such as "CONFIRM LASER." The controller, upon receiving such a command may direct the sensor (see FIG. 1), which may be in a form of a camera mounted in the overhead lights and/or at a base structure for the mechanically-articulable arm to which the light source is attached, to track a position of the target illumination presented by the surgeon-controlled laser spot. The controller, knowing a position of the light structure based on sensing a position in multiple axes of the mechanically-articulable arm, may compare a current position of the light structure with a desired position of the light structure based on the sensor input and command one or more motors in the mechanically-articulable arm to drive the light structure to a position in space that will cause the illumination emitted from the light structure to impinge on the position of the target illumination presented by the surgeon-controlled laser spot. In this manner, the controller may command the light where to move, automatically adjusting the illumination to point precisely where the laser spot is positioned. Typically, in a neurosurgical or cardiovascular operating suite, multiple (three or more) overhead lamps are provided. The control scheme executed by the controller may accept inputs from the surgeon, for example, in a form of voice commands differentiating which one or more of the available light sources the surgeon may select to have moved. In embodiments, the controller may cause sensors in each of multiple overhead lamps to simultaneously, or in sequence, sense a position of the target illumination, and the controller may make a determination regarding which of the multiple overhead lamps may be most appropriately moved to provide the requested illumination based on the position of the target laser spot, and provide a capacity by which to avoid mechanical interference between structures.

Those of skill in the art recognize that particular embodiments for laser tracking exist in many sophisticated systems. The disclosed schemes are intended to particularly adapt a laser spot tracking methodology to a simplified system for hands-free manipulation of a particular component system in a manner that provides a particularly on for seen benefit to users and user systems.

Interaction of the system with, for example, the surgeon will be substantially the same as the surgeon currently wearing a separate illuminating headgear. The head light or surgical loupe is simply replaced, or in embodiments, supplemented by a laser emitting component. The integration of a voice command module and potential inclusion of a microphone as a component of the surgeon's headgear provides additional flexibility and benefit.

As indicated above, no particular configuration to the pointing device, including necessarily being limited to laser sensor, or no particular configuration to the sensing (tracking) element, is to be implied by the above disclosure. Nor is any particular location of the sensor necessarily implied. In embodiments, the sensor may be mounted on the actual apparatus that is being directed, may be mounted on the movable base, or may be mounted in a fixed or movable location otherwise within the environment in which the disclosed system may be operated.

Figure 3:
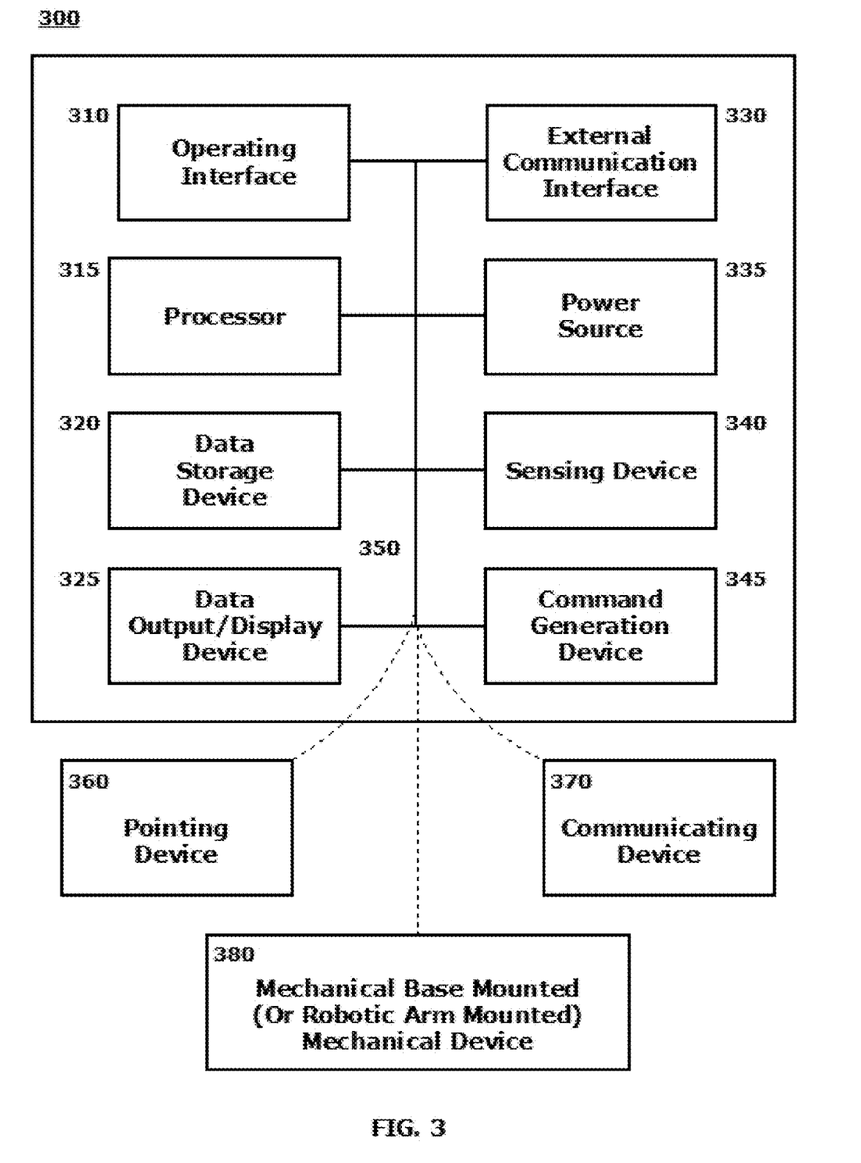
FIG. 3 illustrates a schematic diagram of an exemplary control system for managing and remotely directing movement of mechanically-mounted device according to this disclosure.

FIG. 3 illustrates a schematic diagram of an exemplary control system 300 for managing and remotely directing movement of a mechanical base mounted (or robotic arm mounted) mechanical device 380 according to this disclosure.

The exemplary control system 300 may include an operating interface 310 by which a user may communicate with the exemplary control system 300. The operating interface 310 may be a locally-accessible user interface associated with the mechanical base mounted (or robotic arm out) mechanical device 380. The operating interface 310 may be configured as one or more conventional mechanisms common to control devices and/or computing devices/processors that may permit a user to initiate operations the exemplary control system 300 and input information to the exemplary control system 300 and/or to a controller with which the exemplary control system 300 is associated. The operating interface 310 may include, for example, a conventional keyboard, a touchscreen with "soft" buttons or with various components for use with a compatible stylus, a microphone by which a user may provide oral commands to the exemplary control system 300 to be "translated" by a voice recognition program, or other like device by which a user may communicate specific operating instructions to the exemplary control system 300. The operating interface 310 may be a part of a function of a graphical user interface (GUI) mounted on, integral to, or associated with, the exemplary mechanical device movement system, in a form of a mechanical base mounted (or robotic arm out) mechanical device 380, with which the exemplary control system 300 is associated.

The exemplary control system 300 may include one or more local processors 315 for individually operating the exemplary control system 300 and for carrying into effect sensing, tracking, control and operating functions for the mechanical base mounted (or robotic arm mounted) mechanical device 380 with which the exemplary control system 300 may be associated. Processor(s) 315 may include at least one conventional processor or microprocessor that interprets signal inputs from the sensing device 340 tracking a point of focus of the user-controlled pointing device 360 and voice commands from the user input via a communicating device 370 connected to an external communication interface 330 to particularly control execution of instructions to direct specific functioning of the exemplary control system 300, and control of the movement of the mechanical base mounted (or robotic arm mounted) mechanical device 380 through, for example, operation of a plurality of individual movement devices, proximate to a particular point of focus designated by the operator using a pointing device 360. The individual movement devices which comprise the mechanical base mounted (or robotic arm mounted) mechanical device 380 may include, for example, multiple stepper motors, multiple electro-motive actuators, multiple hydraulic actuators, or various combinations of such actuators, for imparting movement to an implement, in multiple axes, attached to the mechanical base mounted (or robotic arm mounted) mechanical device 380.

The exemplary control system 300 may include one or more data storage devices 320. Such data storage device(s) 320 may be used to store data or operating programs to be used by the exemplary control system 300, and specifically the processor(s) 315 in executing the disclosed mechanical device movement scheme. Data storage device(s) 320 may be used to store information regarding, for example, particular schemes of translational movement for the mechanical device from a current location to a position proximate to a point of focus indicated by a user by aiming the pointing device 360 at that point of focus, the sensing device 340 ascertain a position of device and providing input via the processor 315 for commands to be generated by a command generation device 345 to direct movement of the mechanical base mounted (or robotic arm mounted) mechanical device 380. The data storage device(s) 320 may include a random access memory (RAM) or another type of dynamic storage device that is capable of storing updatable database information, and for separately storing instructions for execution of system operations by, for example, processor(s) 315. Data storage device(s) 320 may also include a read-only memory (ROM), which may include a conventional ROM device or another type of static storage device that stores static information and instructions for processor(s) 315. Further, the data storage device(s) 320 may be integral to the exemplary control system 300, or may be provided external to, and in wired or wireless communication with, the exemplary control system 300, including as cloud-based storage components with which the exemplary control system 300 may communicate.

The exemplary control system 300 may include at least one data output/display device 325, which may be configured as one or more conventional mechanisms that output information to a user, including, but not limited to, a display screen on a GUI of the mechanical base mounted (or robotic arm mounted) mechanical device 380 with which the exemplary control system 300 may be associated. The data output/display device 325 may be used to indicate to a user a status of an in-process movement scheme of the mechanical base mounted (or robotic arm mounted) mechanical device 380 with which the exemplary control system 300 may be associated including an alert as to any impediment in completion of the movement scheme for the mechanical base mounted (or robotic arm mounted) mechanical device 380.

The exemplary control system 300 may include one or more separate external communication interfaces 330 by which the exemplary control system 300 may communicate with communication, control, sensing and other components external to the exemplary control system 300. At least one of the external communication interfaces 330 may be configured as an input port for accepting voice communications from a microphone via the communication device 370 in the manner described above. Any suitable data connection to provide wired or wireless communication between the exemplary control system 300 and external and/or associated components is contemplated to be encompassed by the depicted external communication interface 330.

The exemplary control system 300 may include a power source 335 to provide external power to one or more of the indicated components attached to, or in communication with, the exemplary control system 300. The power source 335 may be in a form of a wired or wireless source for providing one or more of alternating current (AC) or direct current (DC) power to any one or more of the connected devices controlled by the exemplary control system 300.

The exemplary control system 300 may include a sensing device 340, which may be compatible with the pointing device 360 in order to ascertain a point of focus identified by the user through the manipulation of the pointing device 360.

The exemplary control system 300 may include a command generation device 345, which may be a stand-alone device or may be a function of the processor 315. The command generation device 345 determine a static first position of the mechanical base mounted (or robotic arm mounted) mechanical device 380 in multiple axes, determine a commanded position for movement of the mechanical base mounted (or robotic arm mounted) mechanical device 380 according to a positioning of the pointing device 360, and generate control inputs, or commands, for manipulation of the mechanical base mounted (or robotic arm mounted) mechanical device 380 to translate the movement of that device between the two positions according to a particular scheme of movement.

All of the various components of the exemplary control system 300, as depicted in FIG. 3, may be connected internally, and to one or more of a pointing device 360, a communicating device 370, and/or a mechanical base mounted (or robotic arm mounted) mechanical device 380 by one or more data/control busses 350. These data/control busses 350 may provide wired or wireless communication between the various components of the exemplary control system 300, whether all of those components are housed integrally in, or are otherwise external and connected to a mechanical base mounted (or robotic arm mounted) mechanical device 380 with which the exemplary control system 300 may be associated.

It should be appreciated that, although depicted in FIG. 3 as generally an integral unit, the various disclosed elements of the exemplary control system 300 may be arranged in any combination of sub-systems as individual components or combinations of components, integral to a single unit, or external to, and in wired or wireless communication with the single unit of the exemplary control system 300. In other words, no specific configuration as an integral unit or as a support unit is to be implied by the depiction in FIG. 3. Further, although depicted as individual units for ease of understanding of the details provided in this disclosure regarding the exemplary control system 300, it should be understood that the described functions of any of the individually-depicted components may be undertaken, for example, by one or more processors 315 connected to, and in communication with, one or more data storage device(s) 320.

Figure 4:
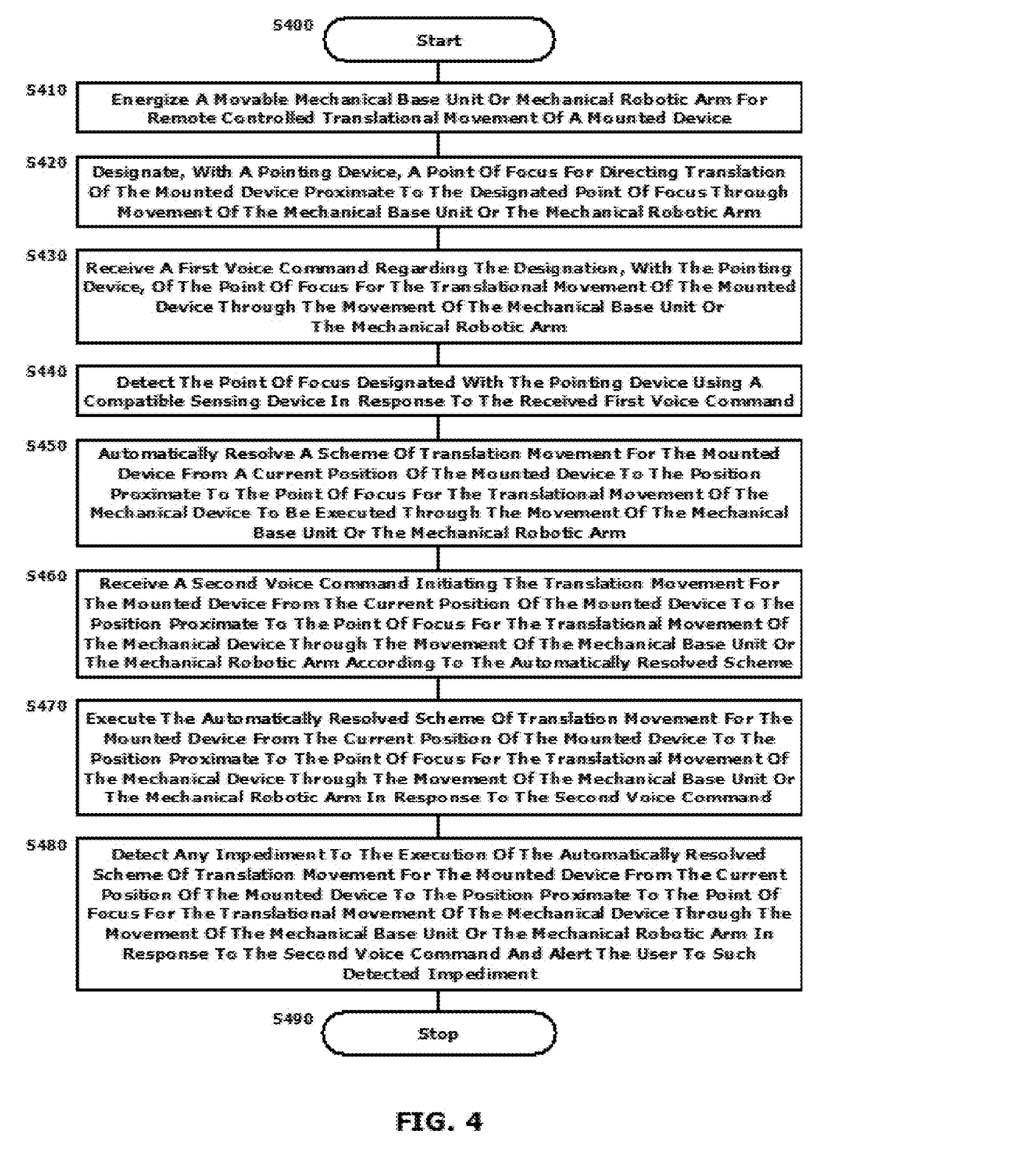
FIG. 4 illustrates a flowchart of an exemplary method for sensing point of focus information regarding a position to which remotely-controlled movement of a mechanically-mounted device may be directed and for implementing movement commands according to the sensed point of focus information employing a control and collision avoidance scheme according to this disclosure.

The disclosed embodiments may include an exemplary method for sensing point of focus information regarding a position to which remotely-controlled movement of a mechanically-mounted device may be directed and for implementing movement and collision avoidance commands for the movement of the mechanically-mounted device. FIG. 4 illustrates a flowchart of such an exemplary method. As shown in FIG. 4, operation of the method commences at Step S400 and proceeds to Step S410.

In Step S410, a movable mechanical base unit or mechanical robotic arm for remote-controlled translational movement of a mounted device may be energized. Operation of the method proceeds to Step S420.

In Step S420, a user may designate, with the pointing device, a point of focus for directing translation of the mounted device proximate to the designated point of focus through movement of the mechanical base unit or the mechanical robotic arm. Operation of the method proceeds to Step S430.

In Step S430, the first voice command may be received regarding the designation, with the pointing device, of the point of focus for the translational movement of the mounted device through the movement of the mechanical base unit or the mechanical robotic arm. Operation of the method proceeds to Step S440.

In Step S440, the point of focus designated with the pointing device may be detected using a compatible sensing device in response to the received first voice command. Operation of the method proceeds to Step S450.

In Step S450, a processor may automatically resolve a scheme of translational movement for the mounted device from a current position of the mounted device to the position proximate to the point of focus for the translational movement of the mechanical device to be executed through the movement of the mechanical base unit or the mechanical robotic arm. Operation of the method proceeds to Step S460.

In Step S460, a second voice command may be received initiating the translational movement for the mounted device from the current position of the mounted device to the position proximate to the point of focus for the translational movement of the mechanical device for the movement of the mechanical base unit for the mechanical robotic arm according to the automatically resolve scheme. Operation of the method proceeds to Step S470.

In Step S470, the automatically resolve scheme of translational movement for the mounted device from the current position of the mounted device to the position proximate to the point of focus for the translational movement of the mechanical device through the movement of the mechanical base unit or the mechanical robotic arm may be executed in response to the second voice command. Operation of the method proceeds to Step S480.

In Step S480, any impediment to the execution of the automatically resolve scheme for translational movement for the mounted device from the current position of the mounted device to the position proximate to the point of focus for the translational movement of the mechanical device through the movement of the mechanical base unit or the mechanical robotic arm in response to the second voice command may be detected. In an event of detection of such an impediment, the translational movement scheme for the mounted device may be halted and a user alerted in order that the user can initiate appropriate action. Such action may include an automated or mechanical override of the scheme of movement to position, or re-position the mechanical device as appropriate. Otherwise, the user may choose to designate another point of focus for the translational movement of the mechanical device by repositioning the pointing device. Any known remedial action by which to bypass the impediment may be employed. Operation of the method proceeds to Step S490, where operation of the method ceases.

The disclosed exemplary systems, methods, schemes and techniques are intended to bring together a number of previously non-integrated automated capabilities to produce a hands-free scheme of movement for an implement, a tool, or a device mounted to a mechanical base or to a distal end of a mechanically-articulated robotic arm. The particular elements that are collected together to implement the disclosed schemes include, but are not limited to, for example, the following:

A laser spot illuminator or other pointing device;

A compatible laser spot or other pointing device seeker or sensor component;

One or more motion sensing input devices, such as, for example, the Microsoft® Kinect, which may include additional components, including but not limited to, (1) an infrared emitter, (2) an infrared depth sensor, (3) a camera, (4) a microphone to support voice commands, (5) a pattern discriminator or color sensor for discerning a particular point of focus designated by the laser spot illuminator or other pointing device;

A processor which may be in a form of an analog to digital converter, which may be usable to translate and transmit data from depth motion sensors to commands for operation of the movable mechanical base or robotic arm;

One or more proximity sensors, which may include a radar-type device, which may be usable to sense and avoid collision of the moving mechanical device with obstructions present in a surrounding environment;

A same or different processor or microprocessor for executing a sensing, movement and collision avoidance scheme in the manner outlined above; and A mechanical movable base, or motorized robotic arm, for carrying into effect the sensing movement and collision avoidance scheme for an attached implement, tool, or device including, but not limited to, and illuminating array or lighting component.

The disclosed schemes are intended to address and/or overcome shortfalls in the related art in which any arguably similar product, often employed to direct mechanical, or semi-automated movement of an attached implement, tool or device may be too expensive, too cumbersome, or otherwise introduce safety, contamination, or other concerns in implementing the tasks which the attached implement, tool or device are intended to support. Using a unique integration of previously unrelated capabilities to achieve the described beneficial outcomes, the systems and methods according to this disclosure are intended to implement a straightforward scheme for hands-free remote control movement of a device, implement or tool mounted on a mechanical movable base structure in a manner that may provide significant improvements over all currently available systems and methods, which may be considered in some way similar to the disclosed schemes. Further, the above-described and other benefits may inure in other operational employments and operational scenarios for the disclosed systems and methods well outside the movement schemes described above. The potential cost savings in measurable and immeasurable efficiencies are boundless.

Specific reference to, for example, the above-discussed embodiments for the disclosed powered systems, devices, schemes, methods, processes and/or techniques for movement of a mechanical device proximate to a particular point of focus as designated by a user-controlled pointing device, and characteristics of the exemplary embodiments specifically directed to use in an operating theater illumination scheme undertaken by a surgeon, or surgical team, should not be interpreted to constrain the disclosed systems, devices, schemes, methods, processes and/or techniques, or any products or product components, to only those embodiments. The depicted and described embodiments are included for non-limiting illustration of the disclosed concepts for implementing these systems, devices, schemes methods, processes and/or techniques for safer, more efficient mechanical device movement in a precise, hands-free, remote controlled operating environment. All of the above depictions and/or descriptions should, therefore, be interpreted as being exemplary only, and not limiting the disclosed schemes, in any manner.

Features and advantages of the disclosed embodiments are set forth in this disclosure and may be, at least in part, obvious from this detailed description, or may be learned by practice of the disclosed embodiments. The features and advantages of the disclosed embodiments may be realized and obtained by means of the instruments and combinations of features particularly described.

The above-described exemplary systems and methods reference certain conventional components and real-world use cases to provide a brief, general description of suitable systems and system operations by which the subject matter of this disclosure may be implemented for familiarity and ease of understanding.

Those skilled in the art will appreciate that other embodiments of the disclosed subject matter may be practiced in many disparate forms and devices of many different configurations.

The exemplary depicted sequence of method steps represent one example of a corresponding sequence of acts for implementing the functions described in the steps of the above-outlined exemplary method. The exemplary depicted steps may be executed in any reasonable order to carry into effect the objectives of the disclosed embodiments. No particular order to the disclosed steps of the method is necessarily implied by the depiction in FIG. 4, except where a particular method step is a necessary precondition to execution of any other method step.

Although the above description may contain specific details, they should not be construed as limiting the claims in any way. Other configurations of the described embodiments of the disclosed systems and methods are part of the scope of this disclosure.

The disclosed schemes represented particular improvement upon currently available voice-actuated system technologies employed, for example, in surgical suites. Using a gestural command methodology via a pointing device such as, for example, a laser pointer, will allow surgeons and surgical staff to significantly and beneficially reduce and amount of time spent in particularly and optimally repositioning lights, and/or other illumination sources, during a surgical procedure. The disclosed schemes may provide precise control of lighting a body cavity without breaking the sterile seal. Ancillary benefits may include reducing an anxiety associated with potentially frustrating requirements to break from a surgical routine to particularly reposition illumination sources, increasing efficiency and safety with respect to the surgical procedures. These benefits may inure in other operational employments and operational scenarios for the disclosed systems and methods well outside the movement of illumination sources in an operating room environment. The potential cost savings in measurable and immeasurable efficiencies are boundless.

It will be appreciated that various of the above-disclosed and other features and functions, or alternatives thereof, may be desirably combined into many other different systems or applications. Also, various alternatives, modifications, variations or improvements therein may be subsequently made by those skilled in the art which are also intended to be encompassed by the following claims.

I claim:

1. A mechanical implement movement system, comprising:
   a base component that is configured to impart movement to an attached implement;
   a movement control device that is configured to generate movement commands to the base component for the movement of the attached implement;
   a pointing device configured to allow a user to designate a point of focus to which the movement of the attached implement is directed; and
   at least one sensor device in communication with the movement control device; the at least one sensor device being configured to detect the point of focus designated by the pointing device as an input to the movement control device,
   the movement control device
      determining an initial position of the attached implement, a final position of the attached implement proximate to the point of focus, and a scheme of movement for the attached implement from the initial position to the final position, and
      generating the movement commands to the base component according to the determined scheme of movement of the attached implement.

2. The mechanical implement movement system of claim 1, further comprising a voice input device in communication with the movement control device, the voice input device being configured to accept user commands for the operation of the movement control device.

3. The mechanical implement movement system of claim 1, the base component being an articulated robotic arm to which the attached implement is secured in a vicinity of a distal end.

4. The mechanical implement movement system of claim 3, the at least one sensor device being mounted to the articulated robotic arm in proximity to the attached implement.

5. The mechanical implement movement system of claim 3, the attached implement being a lighting component.

6. The mechanical implement movement system of claim 1, the pointing device comprising at least one of a point light source or a laser spot generator.

7. The mechanical implement movement system of claim 1, the at least one sensor device comprising a camera for detecting the point of focus designated by the user via the pointing device.

8. The mechanical implement movement system of claim 1, the base component further comprising a plurality of separate electro-mechanical actuators that are individually configured to impart movement to the attached implement in individual axes of movement for the attached implement.

9. The mechanical implement control system of claim 8, each of the plurality of separate electro-mechanical actuators comprising at least one of a stepper motor, an electro-motive actuator, and a hydraulic actuator.

10. The mechanical implement control system of claim 1, further comprising an impediment sensing device that is configured to detect potential collision of the attached implement with an obstruction, the impediment sensing device generating a signal to the movement control device regarding the detected potential collision,
    the movement control device generating at least one of (1) a movement inhibiting command to inhibit further movement of the attached implement according to the scheme of movement, and (2) an alert to the user of the detected potential collision.

11. A method for controlling movement of a mechanical implement, comprising:
    energizing a base component that is configured to impart movement to an attached implement;
    receiving, via at least one sensor, an input regarding a position of a point of focus to which the movement of the attached implement is directed, the at least one sensor detecting a designation of the position of the point of focus by a user directing a pointing device at the designated point of focus;
    determining, with a processor, an initial position of the attached implement;
    determining, with the processor, a final position of the attached implement proximate to the point of focus;
    determining, with the processor, a scheme of movement for the attached implement from the initial position to the final position; and
    generating, with the processor, the movement commands to the base component according to the determined scheme of movement of the attached implement.

12. The method of claim 11, further comprising receiving, with the processor, a voice command from the user via a voice input device, the voice command directing one or more of the steps of the method to be executed by the processor.

13. The method of claim 11, the base component being an articulated robotic arm to which the attached implement is secured in a vicinity of a distal end,
    a generated movement commands directing manipulation of the articulated robotic arm to move the attached implement in multiple axes according to the determined scheme of movement.

14. The method claim 13, the at least one sensor being mounted to the articulated robotic arm in proximity to the attached implement.

15. The method of claim 13, the attached implement being a lighting component, the determined scheme of movement arranging the lighting component to illuminate the point of focus designated by the user with the pointing device.

16. The method of claim 11, the pointing device comprising at least one of a point light source and a laser spot generator,
    the at least one of the point light source and the laser spot generator projecting a point source of light or laser spot at the point of focus designated by the user.

17. The method of claim 16, the at least one sensor comprising a camera for detecting the point source of light or laser spot at the point focus designated by the user.

18. The method of claim 11, the base component further comprising a plurality of separate electro-mechanical actuators that are individually configured to impart movement to the attached implement in individual axes of movement for the attached implement,
    the processor generating individual actuating signals directed to each of the plurality of separate electro-mechanical actuators to execute the determined scheme of movement for the attached implement.

19. The method of claim 18, each of the plurality of separate electro-mechanical actuators comprising at least one of a stepper motor, an electro-motive actuator, and a hydraulic actuator.

20. The method of claim 1, further comprising:

- detecting, with an impediment sensing device, a potential collision of the attached implement with an obstruction, the impediment sensing device generating a signal to the processor regarding the detected potential collision,
- the processor generating at least one of (1) a movement inhibiting command to inhibit further movement of the attached implement according to the scheme of movement, and (2) an alert to the user of the detected potential collision.

\* \* \* \* \*